(12) United States Patent
Ostuni et al.

(10) Patent No.: US 6,893,850 B2
(45) Date of Patent: May 17, 2005

(54) METHOD FOR CELL PATTERNING

(75) Inventors: Emanuele Ostuni, Cambridge, MA (US); Ravi Kane, Troy, NY (US); George M. Whitesides, Newton, MA (US); Rebecca J. Jackman, Boston, MA (US); David C. Duffy, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/808,745

(22) Filed: Mar. 15, 2001

(65) Prior Publication Data

US 2001/0055882 A1 Dec. 27, 2001

Related U.S. Application Data

(60) Provisional application No. 60/190,399, filed on Mar. 17, 2000.

(51) Int. Cl.$^7$ .................. B32B 31/00; C12N 11/08; C12B 11/14
(52) U.S. Cl. .............. 435/174; 435/176; 435/177; 435/178; 435/179; 435/180; 435/182; 435/243; 435/325; 435/395
(58) Field of Search .................. 435/252.1, 174, 435/176, 177, 178, 179, 180, 182, 243, 325, 395, 4, 173.9, 173.4, 173.5, 173.8

(56) References Cited

U.S. PATENT DOCUMENTS

| | | | |
|---|---|---|---|
| 4,022,521 A | | 5/1977 | Hall et al. |
| 4,093,754 A | | 6/1978 | Parsons |
| 4,119,745 A | | 10/1978 | Smith |
| 4,493,757 A | | 1/1985 | Piepers |
| 4,511,599 A | | 4/1985 | Rustomji |
| 4,518,636 A | | 5/1985 | Richards et al. |
| 4,527,988 A | | 7/1985 | Lutz et al. |
| 4,777,117 A | | 10/1988 | Murata et al. |
| 4,871,671 A | | 10/1989 | Errede et al. |
| 4,988,424 A | | 1/1991 | Woodward et al. |
| 5,077,085 A | | 12/1991 | Schnur et al. |
| 5,147,763 A | | 9/1992 | Kamitakahra |
| 5,155,749 A | | 10/1992 | DiMilia et al. |
| 5,160,959 A | | 11/1992 | Everett et al. |
| 5,259,926 A | | 11/1993 | Kuwabara et al. |
| 5,324,591 A | * | 6/1994 | Georger, Jr. et al. |
| 5,480,530 A | | 1/1996 | Zejda |
| 5,486,452 A | | 1/1996 | Gordon et al. |
| 5,510,628 A | | 4/1996 | Georger, Jr. et al. |
| 5,512,131 A | | 4/1996 | Kumar et al. |
| 5,593,814 A | | 1/1997 | Matsuda et al. |
| 5,665,496 A | | 9/1997 | Omika et al. |
| 5,681,661 A | | 10/1997 | Kelly |
| 5,705,043 A | | 1/1998 | Zwerner et al. |
| 5,721,131 A | | 2/1998 | Rudolph et al. |
| 5,776,748 A | * | 7/1998 | Singhvi et al. |
| 5,914,182 A | | 6/1999 | Drumheller |
| 5,948,470 A | | 9/1999 | Harrison et al. |
| 5,976,826 A | | 11/1999 | Singhvi et al. |
| 6,181,144 B1 | | 1/2001 | Hembree et al. |
| 6,207,369 B1 | | 3/2001 | Wohlstader et al. |
| 6,368,838 B1 | | 4/2002 | Singhvi et al. |
| 6,645,432 B1 | | 11/2003 | Anderson et al. |
| 6,686,184 B1 | | 2/2004 | Anderson et al. |
| 6,770,721 B1 | | 8/2004 | Kim |
| 2002/0029814 A1 | | 3/2002 | Unger et al. |
| 2002/0134907 A1 | | 9/2002 | Benett et al. |
| 2003/0156992 A1 | | 8/2003 | Anderson et al. |
| 2004/0027675 A1 | | 2/2004 | Wu et al. |
| 2004/0156988 A1 | | 8/2004 | Mehenti et al. |

FOREIGN PATENT DOCUMENTS

| | | |
|---|---|---|
| DE | 33 31 377 A1 | 3/1985 |
| DE | 38 41 317 A1 | 6/1990 |
| GB | 2 201 637 A | 9/1988 |
| JP | 01 051007 | 9/1990 |
| WO | WO 96/15223 A | 5/1996 |
| WO | WO 99/54786 | * 10/1999 |
| WO | WO 00/60356 A1 | 10/2000 |
| WO | WO 01/70389 A2 A3 | 9/2001 |
| WO | WO 01/89787 A2 | 11/2001 |
| WO | WO 01/89788 A2 | 11/2001 |
| WO | WO 02/084340 A1 | 10/2002 |
| WO | WO 03/062920 A2 | 7/2003 |

OTHER PUBLICATIONS

C.S. Chen et al., "Geometric control of cell life and death," Science, vol. 276, pp. 1425–1428, May 1997.

J.–L. Dewez et al., "Adhesion of mammalian cells to polymer surfaces: from physical chemistry of surfaces to selective adhesion on defined patterns," Biomaterials, vol. 19, pp. 1441–1445, 1998.

A. Folch et al., "Microfabricated elastomeric stencils for micropatterning cell cultures," J Biomed Mater Res, vol. 52, pp. 346–353, 2000.

(Continued)

*Primary Examiner*—David M. Haff
*Assistant Examiner*—Deborah K. Ware
(74) *Attorney, Agent, or Firm*—Wolf, Greenfield & Sacks, P.C.

(57) ABSTRACT

The present invention provides a masking system for selectively applying cells to predetermined regions of a surface. A mask is positioned adjacent to a surface to cover some portions of the surface while allowing other portions of the surface to remain uncovered. Cells then are applied to uncovered portions of the surface and the mask removed. Alternatively, a cell-adhesion promoter is applied to uncovered portions of the surface, and then cells are applied to the surface before or after removal of the mask from the surface. The masking system can be pre-coated, at least on those surfaces which will come into contact with cells, with a cell-adhesion inhibitor to resist absorption of cells and thereby avoid cell damage when the mask is removed (if cells are deposited prior to removal of the mask). A polymeric elastomeric mask that comes into cohesive-conformal contact with a surface to be patterned can be used.

11 Claims, 10 Drawing Sheets

OTHER PUBLICATIONS

M. Mrksich et al., "Using microcontact printing to pattern the attachment of mammalian cells to self–assembled monolayers of alkanethiolates on transparent films of gold and silver," Experimental Cell Research, vol. 235, article No. EX973668, pp. 305–313, 1997.

Anonymous "Lift off technique for high temperature metal depositions," IBM Technical Disclosure Bulletin, vol. 15, No. 7, p. 2305, 1972.

Jackman, Rebecca, et al., "Using Elastomeric Membranes as Dry Resists and for Dry Lift–Off", Langmuir 1999, vol. 15, No. 8, pp. 2973–2984.

Boyden, Stephen, "The Chemotactic Effect of Mixtures of Antibody and Antigen on Polymorphonuclear Leucocytes", Aug. 21, 1961, pp. 453–466.

Astor, Stephen, et al., "Human Leukocyte Migration Inhibition in Agarose Using Four Antigens: Correlation with Skin Reactivity", The Journal of Immunology, vol. 110, No. 4, Apr. 1973, pp. 1174–1179.

Goldstein, G.B., et al. "Studies of the Precipitating Antibody Response in Pulmonary Aspergillosis", Int. Arch. Allergy, vol. 44, 1973, pp. 1–10.

Pratt, Bruce, et al., "Mechanisms of Cytoskeletal Regulation. Modulation of Aortic Endothelial Cell Spectrin by the Extracellular Matrix", AJP, vol. 117, No. 3, Dec. 1984, pp. 349–354.

Cutler, Jim, "A Simple In Vitro Method for Studies on Chemotaxis (38367)", Society for Experimental Biology and Medicine, vol. 147, 1974, pp. 471–474.

Hirschi, Karen, et al., "PDGF, TGF–β, and Heterotypic Cell–Cell Interactions Mediate Endothelial Cell–induced Recruitment of 10T1/2 Cells and Their Differentiation to a Smooth Muscle Fate", The Journal of Cell Biology, vol. 141, No. 3, May 1998, pp. 805–814.

Nelson, Robert, et al., "Chemotaxis Under Agarose: A New and Simple Method for Measuring Chemotaxis and Spontaneous Migration of Human Polymorphonuclear Leukocytes and Monocytes", The Journal of Immunology, vol. 115, No. 6, Dec. 1975, pp. 1650–1656.

Zacchi, Valentina, et al., "In vitro engineering of human skin–like tissue", Biomed. Mater. Res., vol. 40, 1998, pp. 187–194.

Clausen, Jens, "Tuberculin–Induced Migration Inhibition of Human Peripheral Leucocytes in Agarose Medium", Acta Allergologica, 1971, pp. 56–80.

Duffy, David, et al., "Patterning Electroluminescent Materials with Feature Sizes as Small as 5 μm Using Elastomeric Membranes as Masks for Dry Lift–Off", Advanced Materials, vol. 11, No. 7, 1999, pp. 546–552.

Ostuni, Emanuele, et al., "Patterning Mammalian Cells Using Elastomeric Membranes", Langmuir, vol. 16, No. 20, 2000, pp. 7811–7819.

Chiu, Daniel, et al., "Patterned deposition of cells and proteins onto surfaces by using three–dimensional microfluidic systems", Proc. Natl. Acad. Sci., USA, vol. 97, Issue 6, Mar., 2000, pp. 2408–2413.

Z. Bao et al., "High–Performance Plastic Transistors Fabricated by Printing Techniques," Chem. Mater., (1997), vol. 9, pp. 1299–1301.

G.J. Burger et al., "High–resolution shadow–mask patterning in deep holes and its application to an electrical wafer feed–through," Sensors and Actuators, (1996), A54:669–673.

P.E. Burrows et al., "Achieving Full–Color Organic Light–Emitting Devices for Lightweight, Flat–Panel Displays," IEEE Transactions on Electron Devices, (Aug. 1997), V.44, No. 8, pp. 1188–1203.

W.W. Clegg et al., "The preparation of piezoceramic–polymer thick films and their application as micromechanical actuators," Sensors and Actuators, (1997), A58, pp. 173–177.

F. Garnier et al., "All–polymer field–effect transistor realized by printing techniques," Science, (Sep. 16, 1994), V. 265, No. 5179, pp. 1684–1686.

Goldberg, H.D., et al., "Screen printing: a technology for the batch fabrication of integrated chemical–sensor arrays," Sensors and Actuators., B21:171–183 (1994).

V. Golovanov et al., "Different thick–film methods in printing of one–electrode semi–conductor gas sensors," Sensors and Actuators, (1996), B 34, pp. 401–406.

M. Granstrom et al., "Micrometer–and nanometer–sized polymeric light–emitting diodes," Science, (Mar. 10, 1995), V. 267, No. 5203, p. 1479–81.

M. Granstrom et al., "Flexible Arrays of Submicrometer–Sized Polymeric Light Emitting Diodes," Advanced Materials 1995, 7, No. 12.

G. Gustafsson et al., "Flexible sight–emitting diodes made from soluble conducting polymers," Nature, (Jun. 11, 1992), V. 357, pp. 477–479.

T.R. Hebner et al., "Ink–jet printing of doped polymers for organic light emitting devices," Applied Physics Letters, (Feb. 2, 1998), V. 72, No. 5, pp. 519–521.

Y. Kijima et al., "RGB Luminescence from Passive–Matrix Organic LED's," IEEE Transactions on Electron Devices, (Aug. 1997), V. 44, No. 8, pp. 1222–1228.

E.M. Kirschner, "Electronic Chemicals: Lightning–fast electronics market sparks semiconductor chemicals," C&EN, Nov. 24, 1997, pp. 25–39.

S. Leppavuori et al., "A novel thick–film technique, gravure offset printing, for the realization of fine–line sensor structures," Sensors and Actuators, (1994), A 41–42, pp. 593–596.

H. Lorenz et al., "Low–cost technology for multilayer electroplated parts using laminated dry film resist," Sensors and Actuators, (1996), A53, pp. 364–368.

S. Noach et al., "Microfabrication of an electroluminescent polymer light emitting diode pixel array," Appl. Phys. Lett., (Dec. 9, 1996), V. 69, No. 24, pp. 3650–3652.

Y. Mikami et al., "A New Patterning Process Concept for Large–Area Transistor Circuit Fabrication Without Using an Optical Mask Aligner," IEEE Transactions on Electron Devices, (Mar. 1994), V. 41, No. 3, pp. 306–314.

M.L. Renak et al., "Microlithographic Process for Patterning Conjugated Emissive Polymers," Advanced Materials, (1997), V. 9, No. 5, pp. 392–395.

Z. Shen et al., "Three–color tunable, organic light–emitting devices," Science, (Jun. 27, 1997), V. 276, No. 5321, pp. 2009–2011.

K.M. Vaeth et al., "Transition Metals for Selective Chemical Vapor Deposition on Parylene–Based Polymers," Chem. Mater., (2000), vol. 12, pp. 1305–1313.

J. Wang et al., "Identification of a blue photoluminescent composite material from a combinatorial library," Science, (Mar. 13, 1998), V. 270, No. 5357, pp. 1712–1714.

X.–D. Xiang et al., "A combinatorial approach to materials discovery," Science, Jun. 23, 1994, V. 268, No. 5218, pp. 1738–1740.

P. Yam, "Plastics Get Wired," *Scientific American,* Jul. 1995, V. 273, Issue 1.

A.J. You et al., "A miniaturized arrayed assay format for detecting small molecule–protein interactions in cells," *Research Paper,* (Dec. 1997), pp. 969–975.

Jacman, R.J., Wilbur, J.L., and Whitesides, G.M., "Fabrication of Submicrometer Featrues on Curved Substrates by Microcontact Printing", Science, vol. 269, Aut. 4, 1995.

Ostuni, E., Chapman, R.G., Holmlin, R.E., Takayama, S., and Whitesides, G.M., "A Survey of Structure—Property Relationships of Surfaces that Resist the Adsorption of Protein", Langmuir 2001, 17, 5605–5620.

Ostuni, E., Chapman, R.G., Liang, M.N., Meluleni, G., Pier, G., Ingber, D.E., and Whitesides, G.M., "Self–Assembled Monolayers that Resist the Adsorption of Proteins and the Adhesion of Bacterial and Mammalian Cells", Langmuir 2001, 17, 6336–6343.

Kane, R.S., Shuichi, T., Ostuni, E., Ingber, D.E., and Whitesides, G.M., "Patterning Proteins and Cells Using Soft Lithography", Biomaterials 20 (1999) 2363–2376.

Jackman, R.J., Duffy, D.C., Ostuni, E., Willmore, N.D., and Whitesides, G.M., "Fabricating Large Arrays of Microwells with Arbitrary Dimensions and Filling Them Using Discontinuous Dewetting", Analytical Chemistry, vol. 70, No. 11, Jun. 1, 1998.

Jackman, R.J., Brittain, S.T., Adams, A., Wu, H., Prentiss, M.G., Whitesides, S. and Whitesides, G.M., "Three–Dimesional Metallic Microstructures Fabricated by Soft Lithography and Microelectodeposition", Langmuir 1999, 15, 826–836.

Ostuni, E., Chen, C.S., Ingber, D.E., and Whitesides, G.M., "Selective Deposition of Proteins and Cells in Arrays of Microwells", Langmuir 2001, 17, 2828–2834.

* cited by examiner

ADD BSA SOLUTION

1. RINSE WITH PBS
2. PEEL MEMBRANE AND TRANSFER TO CLEAN SUBSTRATE

INCUBATE WITH FN

EXPOSE TO 1ST CELL TYPE

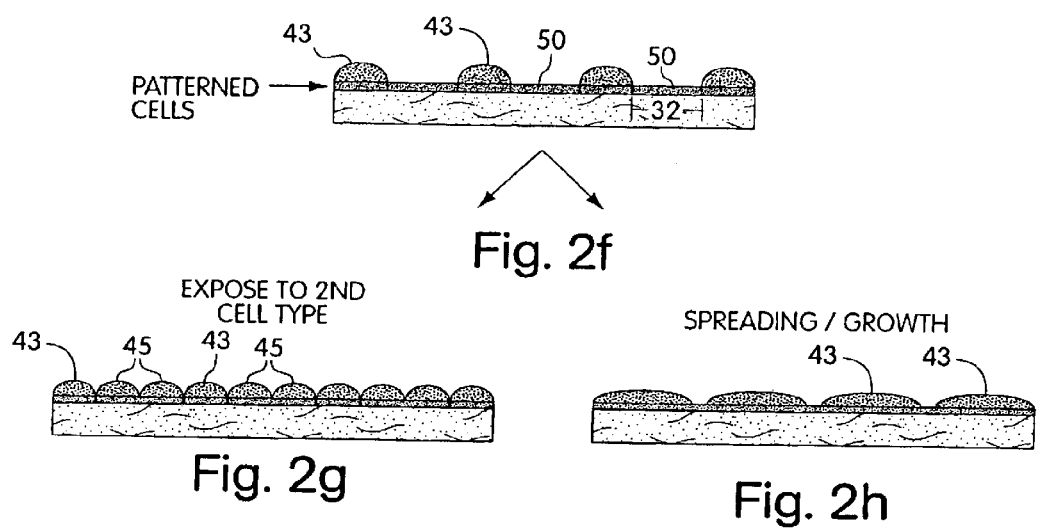

100 μM

250 μM, A-B

100 μM, C-D

300 μM, E

METHOD FOR CELL PATTERNING

RELATED APPLICATIONS

This application claims priority to U.S. Provisional Patent Application Ser. No. 60/190,399, filed Mar. 17, 2000, entitled CELL PATTERNING VIA AN ELASTOMERIC MASK.

This invention was sponsored by NSF Grant Nos. PHY-9312572, DMR-9809363, ECS-9729405 and AFOSR/SPAWAR Grant No. N66001-98-1-8915. The government has certain rights in the invention.

FIELD OF INVENTION

The present invention relates to methods for patterning cells on substrate surfaces via an elastomeric mask. These methods allow for the study of cell migration and growth.

BACKGROUND OF THE INVENTION

Cell adherence on substrate surfaces, particularly surfaces used for cell-culture such as glass or plastic, is necessary in many instances for the study of cells in furthering applications such as tissue engineering, biosensors, etc. Cell patterning, i.e. placing cells in discrete portions of a surface, has been provided by photolithography. Although the technology of photolithography is very highly developed, it presents several disadvantages. Photolithography presents harsh conditions which can destroy the cells themselves. Clean-room facilities and other complex equipment are also required and such facilities and equipment are not readily accessible to most biologists. Photolithography is not amenable to controlling the molecular properties of a surface required for many sophisticated cell-biological experiments. In addition, photolithography modifies a surface only at the beginning of an experiment. Once cells are deposited, photolithography cannot be used to make further surface modifications.

Laminar flow (FLO) patterning involves surface modification via laminar flow of adjacent fluid streams with low Reynolds numbers. FLO patterning is restricted to simple patterning and thus is useful for patterning the environment of a cell and for cell labeling. This technique, however, is not suited for patterning the shape and size of the cells.

Accordingly, there is a need to pattern cells in a facile manner while subjecting the cells to relatively mild conditions.

SUMMARY OF THE INVENTION

One aspect of the present invention provides a method for patterning cells. The method involves shielding a first portion of a surface of an article with a masking system. The masking system comprises a cohesive mask in conformal contact with a surface of the article. The method also involves applying an agent to a channel within the masking system to a second portion of the surface of the article while preventing application of the agent to the first portion of the surface of the article. The method also involves applying cells onto the agent.

Another aspect of the invention provides a method for patterning cells comprising shielding a first portion of a surface of an article with a masking system. The masking system comprises a cohesive mask in conformal contact with the surface of the article. The method further involves applying a cell-adhesion inhibitor through a channel within the masking system to a second portion of the surface of the article while preventing application of the cell-adhesion inhibitor to the first portion of the surface of the article.

Another aspect of the present invention provides a method for patterning cells comprising shielding a first portion of a surface of an article with a masking system. The masking system comprises a cohesive mask in conformal contact with the surface of the article. The method further involves applying a cell-adhesion promoter through a channel within the masking system to a second portion of the surface of the article while preventing application of the cell-adhesion promoter to the first portion of the surface of the article.

Another aspect of the present invention provides a method for patterning cells comprising providing an article having a first pattern of cells of a first type. The method also involves applying an agent to a portion of a surface of the article, the portion being contiguous with the first pattern.

Another aspect of the present invention provides an article comprising a first pattern of cells of a first type contiguous with a second pattern of cells of a second type.

Another aspect of the present invention provides a method comprising shielding a first portion of a surface of an article with a masking system. The method involves allowing a cell-adhesion promoter to be applied to a second, unshielded portion of the surface of the article while preventing application of the cell-adhesion promoter to the first portion of the surface of the article with the masking system. The method further involves applying a cell to the second portion of the surface.

Another aspect of the present invention provides a method for patterning cells comprising shielding a first portion of a surface of an article with a polymeric masking system. The method involves applying an agent to a channel within the masking system to a second portion of the surface of the article while preventing application of the agent to a first portion of the surface of the article. The method further involves applying cells onto the agent.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION

Figure 1A:
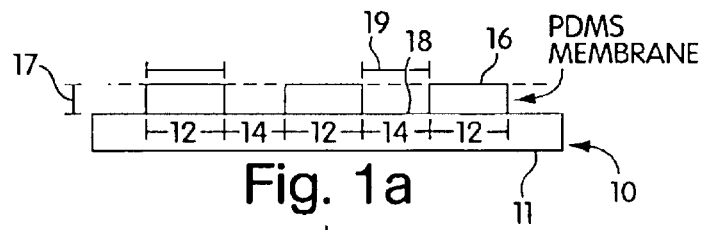
FIG. 1 shows a schematic diagram of lift-off membrane (masking system) patterning to pattern cells onto a surface of an article according to the invention.
Figure 1B:
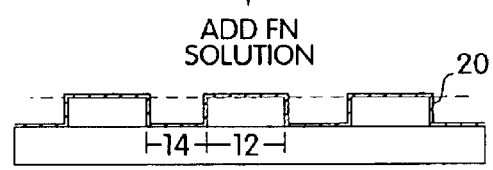
Figure 1C:
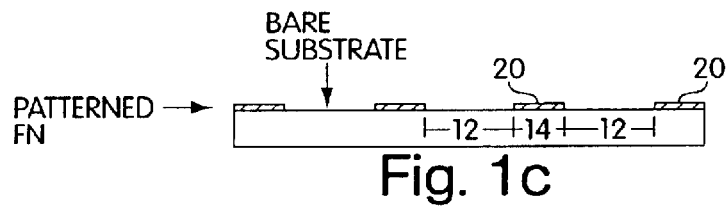

The present invention provides methods for patterning cells involving a masking system, and surfaces modified optionally using the system. The methods are particularly advantageous in that various cell patterns can be provided without the aid of photolithographic steps and thus patterns can be achieved in a relatively simple and inexpensive manner. The present invention is applicable for patterning cells on a broad range of substrates, which include most materials routinely used in cell culture. The masking system has flexibility for patterning on substrates of essentially any shape, and has rigidity to be reused a number of times.

A resulting pattern of cells can be used for a variety of applications including observing cell growth and spreading, chemotaxis, haptotaxis, morphogenesis, and the patterning of multiple cell types. In addition, cell patterning can have long range applications in the study of regeneration, partial regeneration or healing of human organs and wounds, i.e. tissue engineering. Other applications involve biosensors.

One aspect of the present invention provides a method for patterning cells. One method involves shielding a first portion of a surface of an article with a masking system. Subsequently, a second, unshielded portion of the surface of the article is exposed to an agent such as a cell-adhesion promoter, a cell-adhesion inhibitor, or a cell, before or after removal of the masking system. The masking system can be polymeric and, in one embodiment, the masking system comprises a mask having a flexible surface which allows the mask to conform to the surface. By "conform" it is meant to define essentially continuous contact between the masking system and the portions of the article to be patterned. This embodiment is to be distinguished from, for example, a metal screen or a rigid polymer, each of which can contact a surface to be masked but which may not be flexible enough to conformally contact the surface. The flexibility of the mask can be provided by the use of an elastomeric mask. The mask can be made of a polymeric material such as polydimethylsiloxane (PDMS), or the like. In one embodiment, the mask can shield selected portions of the surface by being brought into contact with those portions. Due to the flexibility of the mask, the surface can be either a planar or non-planar surface.

In one embodiment, there is a channel within the masking system, and preferably a plurality of channels within the masking system. The masking system can comprise first and second opposing surfaces where the channel passes through the mask, connecting the first surface with the second surface. The channel can function to expose certain portions (a second portion) of the surface of the article, whereas a first portion of the article is shielded due to conformal contact of the article with the masking system. In one embodiment, the first portion is contiguous with the second portion. In one embodiment, a channel within the mask is a hole through the mask, and by placing one surface of the mask onto a substrate, wells are formed as defined by the walls of the channel and the substrate surface (second portion of the surface). The mask can contain a variety of liquid or solid agents within these wells.

In one embodiment, the mask is a polymer. A preferred polymer is a polymeric elastomer that can form a seal against the surface of the article. "Seal" in this context means that when the mask is sealingly engaged with a surface and a fluid is applied to the masked surface, the fluid is allowed to contact only those portions of the masked surface in register with channels of the mask and the fluid does not pass under the mask and contact shielded portions of the article surface covered by solid portions of the mask, so long as the fluid does not degrade the mask or the surface to be patterned (in which case fluid could pass under the mask due to degradation of the mask and/or surface). For example, the seal can prevent a protein solution from seeping under the mask. "Sealing" in this context is to be distinguished from the operation of other rigid or flexible masks that may be brought into conformal contact with a surface, but that can not seal against the surface. It is a feature of the invention that masks of the invention can form a seal against a substrate surface in the absence of any clamping apparatus or other apparatus used to apply a force against the mask in a direction of the substrate surface. Where elastomeric surfaces are used, and the elastomeric surface and substrate surface to be masked are clean, sealing can occur essentially instantaneously upon contact without application of significant pressure, and sealing can be maintained without maintenance of any pressure. This sealing is reversible, that is, the mask can be removed from the substrate surface by being peeled off, and can be reused on the same or a different substrate surface. Reusability of a particular mask increases with the thickness of the mask.

Exemplary techniques for fabricating a mask are described in PCT publication WO 99/54786, entitled "ELASTOMERIC MASK AND USE IN FABRICATION OF DEVICES, INCLUDING PIXELATED ELECTROLUMINESCENT DISPLAYS," by Jackman et al., published Oct. 28, 1999, and which is incorporated herein by reference. For example, a flexible mask can be created by a number of polymerization methods. One method, described in PCT publication WO 99/54786, involves spin-coating a pre-polymer layer onto a substrate surface having an array of cylindrical posts.

In one embodiment, the method involves applying an agent through the channel. The method allows the agent to contact the exposed (second) portion of the surface of the article while preventing application of the agent to the shielded (first) portion of the article. The agent can be applied via deposition, chemical reaction, or the like. For example, if the agent is provided as a solution, the deposition can involve spraying or dripping the solution onto the mask and through the channel, or dipping the entire substrate and masking system assembly into the solution. In one embodiment, a vacuum may be applied to remove any air bubbles within the solution in the channel to ensure optimal surface coverage.

In one embodiment, the agent has physical and/or chemical properties that allow its adherence to the surface of the article via adsorption. Application of agent can result in chemical reaction resulting in covalent or ionic interactions between the surface of the article and the agent.

In one embodiment, the agent can be a cell-adhesion promoter, i.e. the agent can have physical (e.g., "sticky" materials) and/or chemical properties that allow cell adherence to the agent while maintaining the integrity of the cell, and the method involves applying cells onto the agent. Cell adhesion can be achieved by specific or non-specific interactions. Surfaces which promote non-specific interactions adhere most cells. Examples of such surfaces include ionic or charged surfaces. Hydrophilic surfaces also promote non-specific cell adhesion. An example of a surface involved in non-specific interactions include polymer surfaces used in biomaterials such as polylysine or plasma-treated polystyrene. Cell-specific interactions generally result when a cell has a receptor which recognizes certain surfaces. For example, mammalian cells have receptors which recognize extracellular matrix proteins. Thus, cells can be patterned onto surfaces using masking systems of the invention by first applying a cell-adhesion promoter agent to the surface, preferably using a masking system, or applying a masking system to a surface which already is cell-adhesion promoting. Both cell-adhesion promoting agents and cell-adhesion promoting surfaces are well-known in the art (some of which are described immediately above). Examples of cell-adhesion promoting agents include extracellular matrix proteins such as vitronectin, laminin, fibronectin, collagens and gelatins. Alternatively, a surface can be modified with antibodies which recognize certain cellular receptors. Cell-adhesion inhibiting surfaces and cell-inhibiting agents also are well-known. Examples of cell-adhesion inhibiting agents include polyethylene glycol-based agents. Those of ordinary skill in the art can easily screen surfaces for their natural cell-adhesion promoting or inhibiting characteristics, or agents for cell-adhesion promotion or inhibition as follows. Various untreated surfaces can be studied, or various agents can be applied to surfaces, cells can be applied to those surfaces, and the ability of the cells to adhere to the surface can be studied via morphology or other characteristics. This is routine for those of ordinary skill in the art.

In one embodiment, the article or surface of the article can be a metal oxide such as silica, alumina, quartz, glass, and the like or derivatives thereof, or metals such as gold, silver and copper. The surface can be derivatized with functional groups including amides, carboxylic acids, phosphoryl groups, hydroxyl groups, amino acid groups, amines, sulfonyl groups. Oxy compounds or plastics can also be used in accordance with the present invention. Additional materials and functional groups can be found in U.S. Pat. No. 5,512,131, issued Apr. 30, 1996 and incorporated herein by reference. In one embodiment, the surface can be that of an article typically used to study cells, such as a microscope slide, petri dish, test tube or other articles. Typically, these articles are made of polystyrene, glass or polycarbonate. Functional groups discussed above, and other functionality can be provided on the surface by coating the surface with a self-assembled monolayer as described in U.S. Pat. No. 5,512,131. Self-assembled monolayers are well-known and typically involve molecules each including a group that adheres to a surface and a spacer moiety that can assemble, or pack with other spacer moieties such that when a plurality of the molecules are exposed to a surface they orient themselves in an ordered manner with the groups that adhere to the surface against the surface and the spacer moieties packed relative to each other and extending from the surface. At the other end of each, or selected of these molecules can be provided functional groups providing the exposed portion of the self-assembled monolayer with a desired chemical functionality.

FIG. 1 shows a schematic diagram of one example for patterning agents associated with cell deposition, according to the present invention. FIG. 1(a) shows an article 10 having a surface 11 with a first portion 12 and a second portion 14. A masking system can comprise a mask 16. Mask 16 (shown in cross section) is brought into conformal contact with the surface of article 10 such that the first portion 12 of surface 11 is shielded. FIG. 1(b) shows the results of applying an agent 20 through channel 18 of masking channel 16. Because mask 16 shields first portion 12, agent 20 is applied only to second portion 14 and is prevented from being applied to first portion 12. Agent 20 can be a cell-adhesion promoter (e.g., fibronectin). Cells can be applied onto agent 20 on second portion 14 at this stage. Cells, however, will also adhere to all surfaces coated by agent 20 (e.g., see FIG. 5A). Alternatively, mask 16 can be removed prior to applying cells onto agent 20, as shown in FIG. 1(c). In FIG. 1(c), substrate 10 has a pattern of agent 20 on second portion 14, whereas first portion 12 comprises a surface free of agent 20 (e.g., see FIG. 6A).

Figure 1D:
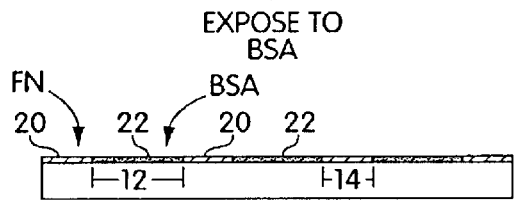
Figure 1E:
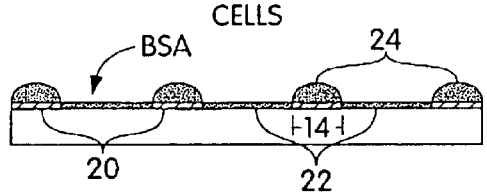

FIG. 1(d) shows the results of adding a second agent 22 to the exposed first portion 12. Second agent 22 can be a cell-adhesion inhibitor, such as bovine serum albumin. Due to the inability of cells to adhere to a cell-adhesion inhibitor, a cell-adhesion inhibitor functions to localize the deposition of cells to a confined area, specifically portion 14. Generally, cells will not grow or spread onto a surface that comprises a cell-adhesion inhibitor. By adding cells 24 to the surface of FIG. 1(d), a pattern of cells can be established in register with portions 14, as shown in FIG. 1(e) (e.g., see FIG. 6B).

FIG. 1 demonstrates that with techniques of the invention material can be patterned through the holes against the substrate, and the mask removed, leaving an array of pixels, without the requirement of steps and apparatus involved in laser ablation, photolithography, and shadow mask procedures.

As discussed more fully below, in one embodiment cells can be deposited onto portion 14 while mask 16 is on surface 11 providing that the cells do not adhere to the mask or have been subjected to a pre-coating treatment (e.g., see FIG. 2 and discussion). The amount of cells deposited in each channel can depend on factors such as the diameter and height of the channels or the density of cells in a fluid suspension. Each channel may contain one cell or several tens of cells. An advantageous feature of the invention is that cell(s) are confined to the space defined by the channel until mask 16 is removed from article 10. Depending on the number of cells to be deposited, the channels or holes of the mask can have a diameter of less than about 1 mm, less than about 500 μm, less than about 250 μm, less than about 100 μm, less than about 50 μm, less than about 25 μm, less than about 10 μm, less than about 5 μm, down to less than about 1.5 micron.

Any pattern of channels 18 in the mask, for example a pattern defined by a single channel or many channels that can be circular, oval, square, rectangular, and the like, and arranged in a grid-like array (as illustrated) or a non-array (for example random pattern) can be used.

The mask and channels can be of a variety of dimensions. In one embodiment, the mask has a thickness of no more than about 1 mm, preferably no more than about 500 μm, more preferably no more than about 200 μm, preferably no more than about 100 μm, more preferably still no more than about 25 μm. In one embodiment, channel 18 has a preferred cross-sectional dimension 19 that corresponds to a thickness 17 of the mask 20 to create a length to diameter ratio of channels of no more than about 5 to 1, and preferably no more than about 2 to 1. Of course, the number of channels and the shape of channels can be varied by any method known to one of ordinary skill in the art.

The conformal contact of mask 16 with article 10 should be strong enough to prevent slippage of the mask on the article surface yet capable of being removed by a peeling process. In one embodiment, the mask has a thickness of at least about 50 μm. This thickness helps ensure the integrity of the mask through several peeling processes. Preferably, the peeling should not disturb the integrity of the pattern. It is a feature of the invention that the mask is cohesive and can be removed from a surface as a single unit and re-used, i.e., the mask facilitates a "dry lift-off" procedure. The mask is cohesive in that attractive forces within the mask that hold the mask together are stronger than forces typically required to remove the mask from a surface. That is, the mask can be used to seal a surface during a deposition process, then can be removed by lifting a portion of the mask which draws the entire mask away from the surface, and the mask then can be reused. This is to be distinguished from a lithographically-created mask such as a photoresist mask. Use of a cohesive mask of the invention allows formation of the mask on the surface to be masked without degrading, at the surface, portions defining channels 32 (such as are degraded in creation of a lithographically-created mask).

Alternatively, agent 20 is a cell-adhesion inhibitor, and upon removal of mask 16, a cell-adhesion promoter can be applied to the bare surface to achieve the arrangement of FIG. 1(d).

To describe FIG. 1 with a specific example, a PDMS mask (i.e., masking system 16, alternatively referred to as a membrane) is used as a resist against the adsorption of the cell-adhesion promoter fibronectin (FN, an extracellular matrix protein) to the surface of the substrate. FN adsorbs only to the surface of the substrate that is exposed by the pores of the membranes (see FIG. 6). Removal of the mask from the surface generates a pattern of FN. The substrate is then exposed to bovine serum albumin (BSA)-containing culture media to ensure that the remainder of the surface is coated by a protein that resists cell attachment. Cells from a suspension adhered to this substrate only in the pattern defined by the pores of the membrane (see FIG. 7). FIG. 1 is not drawn to scale and FIG. 1 does not imply that layers of BSA and FN have the same thickness. The mask features may be curved at the top as a result of menisci formation during spin coating or other processes.

For certain cell types, it may be preferable to pattern the cells by confining the cells within mask channels. The mask channels provide a physical barrier to contain and thus maintain control of cell size and shape, or the size and shape of a layer of cells. In this embodiment, ideally, a mask is positioned on the surface to create certain wells as defined by mask channels and the surface, and cells are deposited into these wells. Because the mask itself may have cell-adherent properties, however, removal of the mask may result in tearing of cell walls in some instances, particularly where cells are adhered simultaneously to the mask and the substrate. Accordingly, to ensure that contacting the cells with the mask will not damage cell walls upon mask removal, in one embodiment, a cell pattern is provided by use of a pre-coated mask. At least a portion of the mask, preferably those portions that could contact cells in the process, can be pre-coated with an agent that is a cell-adhesion inhibitor, such as bovine serum albumin. Thus, a cell does not have a tendency to adhere to the mask and peeling off the mask does not damage the cells.

FIG. 2 shows an example for patterning cells involving a pre-coating treatment of the masking system. FIG. 2(c) shows an article 30 having a surface 31 comprising a first portion 32 and a second portion 34. Mask 36 (shown in cross section) shields first portion 32 by being in conformal contact with first portion 32 whereas channels 38 expose second portion 34. FIG. 2(c) also shows a coating of a first agent, a cell-adhesion inhibitor agent 40 which has been applied only to exposed surfaces of mask 36 and not on exposed surfaces of second portion 34 of article 30. Addition of a second agent 42, such as a cell-adhesion promoter, provides a coating over second portions 34 of article 30, as shown in FIG. 2(d). Preferably, agent 40 is selected to resist adsorbtion of agent 42. The addition of cells 43 results in cell adhesion on agent 42 only, and cell adhesion is inhibited on surfaces covered by agent 40, as shown in FIG. 2(e) (e.g., see FIG. 5B). The arrangement shown in FIG. 2(e) provides the advantage that upon peeling the masking system 36 from article 30, the cell-adhesion inhibitor nature of the surface of article 36 coated with agent 40 will reduce any friction between masking system 36 and the cells, thus promoting cell integrity (e.g., see FIG. 8).

Figure 2A:
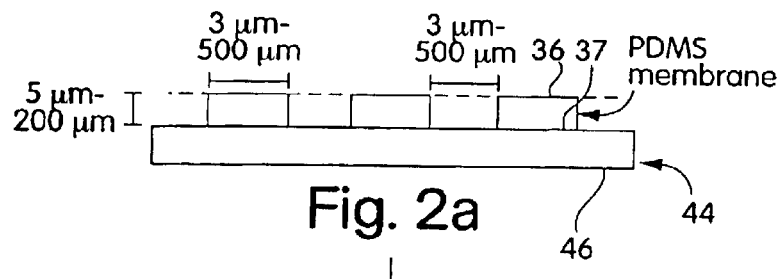
FIG. 2 shows a schematic diagram for lift-off membrane patterning involving a pre-coated masking system according to the invention.
Figure 2B:
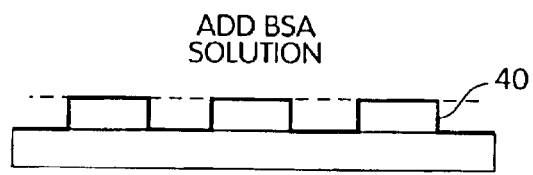
Figure 2C:
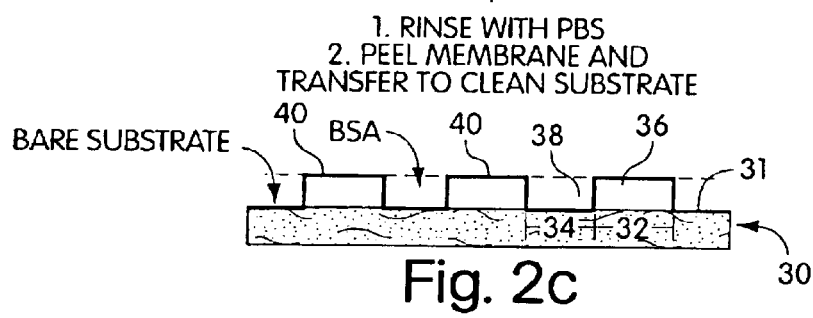
Figure 2D:
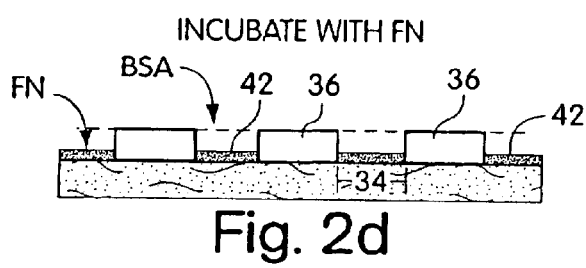
Figure 2E:
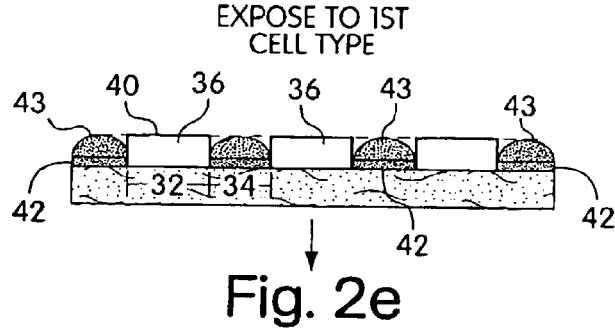

In this embodiment, article 36 can be pre-coated with a cell-adhesion inhibitor 42 as shown in FIGS. 2(a) and (b). In FIG. 2(a), a first surface 37 of mask 36 is contacted with a surface 46 of substrate 44. Preferably, first surface 37 is brought into conformal contact with surface 46. FIG. 2(b) shows the results of coating agent 40 (a cell-adhesion inhibitor) onto mask 36 and substrate 44. Surface 37 of mask 36 is free of the agent 40. Removal of mask 36 from substrate 44 followed by placement of mask 36 on surface 31 of article 30 results in unexposed surfaces (second portions 34) of article 30 free of agent 40. Subsequently, mask 36 can be used to shield portions of article 30, as shown in FIG. 2(c).

FIG. 2(f) shows the results of removing mask 36 from article 30, exposing first portions 32, followed by application of agent 50 (either a cell-adhesion inhibitor or promoter) to first portions 32. Where agent 50 is a cell-adhesion promoter, the cells applied onto agent 42 can be allowed to spread onto agent 50, the results of which are shown schematically in FIG. 2(h). Thus, the invention provides a novel medium to study the effects of cell spreading, or other cellular phenomena, such as chemotaxis, haptotaxis or morphogenesis from a predetermined area (i.e., shape and size) of an individual cell to groups of cells.

It can be seen that in this aspect of the invention, a method is provided for a simple and inexpensive method to grow attached cells within patterned constraints. In one embodiment, the constraints can be released to allow the cells to spread. Most current techniques for patterning cells are not directly compatible with a process that requires the cells to be grown within patterned constraints, and then releasing those constraints and allowing the cells to migrate. Patterning of cells is an experimental tool that can be useful, for example, for studying and controlling the behavior of anchorage-dependent cells. Patterning of cells has been previously achieved with microcontact printing (see for example, C. S. Chen et al. *Science* 1997, 276, 1425–1428; R. Singhvi et al. *Science* 1994, 264, 696–698; *Prog.* 1998, 14, 378–387; G. P. Lopez et al. *J. Am. Chem. Soc.* 1993, 115, 5877–5878; A. Kumar et al. *Appl. Phys. Lett.* 1993, 63, 2002–2004; M. Mrksich et al. *Trends Biotech.* 1995, 13, 228–235). Although microcontact printing is an experimentally convenient technique that has sufficient resolution to allow the patterning of single cells, in its simplest configuration it does not allow the cells to be "released" from the pattern; that is, once a pattern of SAMs has been formed, fibronectin adsorbed, and cells attached, there is no practical way of changing the pattern or allowing the cells to spread beyond the boundaries of this pattern. Other patterning methods involve more complex processes.

In another embodiment, agent 42 is a first cell-adhesion promoter and agent 50 is a second cell-adhesion promoter. This embodiment provides a method for patterning multiple cell types onto a single substrate in which cells of a second type can be applied onto agent 50. In one embodiment, the first cell-adhesion promoter is specific for cells 43 of a first type and the second cell-adhesion promoter is specific for cells 45 of a second type (FIG. 2(*g*)).

FIG. 2 can be described with reference to a specific example. The mask 36 is pre-coated with agent 40, namely BSA, selectively on one of its sides and in interior channel surfaces and the pre-coated mask is used during the adsorption of FN to a clean substrate surface (FIG. 2*d*). Cells adhere to the surface of the substrate that is coated with FN while being prevented from adhering to the walls of the membrane channels or the top of the mask, coated with BSA. Accordingly, upon peeling, the mask does not damage the cells that remain attached to the surface of the substrate in the pattern defined by the holes of the membrane (see FIG. 2F, FIG. 8). Removal of the mask exposes a pattern of cells adjacent exposed portions of the surface. The protected areas of the substrate can then be modified by the adsorption of an adhesive protein that allows the patterned cells to spread to the exposed surface. Alternatively, another cell type can be adhered to the surface. Upon removal of mask 36, cell integrity can be tested via a fluorescence assay. In this assay, cells are incubated with a dye (e.g., propidium iodide) which diffuses only into cells which have damaged membranes and which become more fluorescent upon complexing with DNA.

Alternately, the mask can be prepared of a material that does not adhere cells. Thus, a pre-coating step is unnecessary. The material of the non-adherent mask can depend on the cell-type.

More than two cell types can be patterned on a single surface, by controlled shielding of various portions of the article. As described in PCT publication WO 99/54786, masking systems involving multiple masks can be used in differing overlaying arrangements to control the application of particular agents or cell types into desired portions of the surface.

It is a feature of the invention that mask/surface systems provide methods for observing cell growth when cells are initially deposited within a physically-constrained barrier. Cells can be grown within the wells as defined by mask channels and the substrate surface. Surface chemistry of the mask walls and substrate surface can be controlled in a way to cause cells to attach and spread on the substrate but not attach to the mask. The mask can then be removed to allow cells to spread onto the rest of the surface.

Another advantageous feature of the invention is the provision of channels that are of sufficiently small size to control the size and shape of a single cell. The physical constraints can be used to inhibit cell growth while the mask is conformed to the substrate and subsequently promote cell growth upon removal of the mask from the substrate. Known techniques for studying cell spreading and migration typically have not involved controlling the shape and size of cells before allowing them to spread and migrate. The shape and size of cells determines their passage through the cell cycle. It is known that a cell growth involves a cycle of stages. A cell may not attain the next stage until it has reached a certain size. The size and shape of cells may not only affect their ability to spread, but ultimately the ability to migrate about a surface. The ability to control cell growth and migration has many applications in the control of wound healing, cell death (apoptosis) and differentiation. Angiogenesis (capillary growth) is one example of the differentiation of bovine capillary endothelial cells. A channel can be used to constrict the cell to a specific size, whereupon removal of the channel results in cell growth and thus the control of cell migration about the substrate surface or a portion of the substrate surface.

It is to be understood that the order of steps for shielding via the masking system, application of agents and application of cells can be varied to obtain a desired result. For example, another aspect of the invention provides a method for patterning cells, comprising shielding a first portion of a surface of an article with a masking system comprising a cohesive mask in conformal contact with the surface of the article. The method involves applying a cell-adhesion inhibitor through a channel within the masking system to a second portion of the surface of the article while preventing application of the cell-adhesion inhibitor to the first portion of the surface of the article. Referring back to FIG. 1, this aspect presents a different result from that described previously for FIG. 1(*c*), namely second portions 14 having a cell-adhesion inhibitor applied thereon, and exposed first portions 12. This aspect describes a different method for obtaining the result shown in FIG. 1(*d*).

Another aspect of the invention provides a method for patterning cells, comprising providing an article having a first pattern of cells of a first type and applying an agent to a portion of the surface of the article. This portion can be contiguous with the first pattern. In one embodiment, the agent can be a cell-adhesion inhibitor for cells of the first type. In another embodiment, the agent is a cell-adhesion promoter for cells of a second type. This method is advantageous in the patterning of multiple cells or for methods allowing cell spreading, where the affinity of the different cell-adhesion promoters is not strong enough to differentiate between cell types to a desired extent. Thus, by adhering cells of a first type to the first cell-adhesion promoter prior to applying the second-adhesion promoter onto the surface, greatly differing affinities of different cell-adhesion promoters is not as critical a requirement to provide discrete patterns of multiple cell types.

The ability to pattern multiple cell types has applications in organ regeneration. For example, it is known that certain organ types have striated patterns of different cell types. For example, a surface may have one continuous portion of cells of a first type adjacent a continuous portion of cells of a second type which in turn is an adjacent another portion of cells of a first type or even a third type. The continuous portion may resemble a layer of any shape running parallel to the substrate surface. Thus, there is a need to control the positioning of cells of a first type with respect to cells of a second type. For some cases, the cells of the first type do not have greatly differing affinities for surface adherence than the cells of the second type. Such close affinities may present strategic difficulties in that one surface (or agent on the surface) can adsorb significant quantities of cells of either type. The flexible mask of the present invention shields certain portions of the substrate surface indiscriminate of cell affinities, and thus, the need to fine-tune cell-substrate affinity is circumvented. For the above example, the striated layers of cells can be provided by a mask having channels shaped to have an extremely long length but short widths. Of course, the shape of the channels do not have to resemble a regular geometrical shape, and can be of any shape feasible that can withstand the coating, depositing and peeling processes.

Another aspect of the present invention provides an article comprising a first pattern of cells of a first type contiguous with a second pattern of cells of a second type. This aspect is to be distinguished from a random array of cells of multiple types. The article can have more than two patterns of different cell types by using the methods described herein.

The function and advantage of these and other embodiments of the present invention will be more fully understood from the examples below. The following examples are intended to illustrate the benefits of the present invention, but do not exemplify the full scope of the invention.

General Conditions

Materials.

SU-8 50 photoresist was supplied by Microlithography Chemical Corp. (Newton, Mass.). We used rigid chrome masks (Advanced Reproductions, North Andover, Mass.) or transparencies as the photomasks in the photolithographic step. Poly(dimethylsiloxane) (PDMS); Sylgard 184) was obtained from Dow Corning (Midland, Mich.). Bacteriological and tissue culture grade Petri dishes were purchased from Falcon. No. 2 glass slides from Corning Inc. (Corning, N.Y.) were used as received. Silicon wafers <110> were obtained from Silicon Sense Inc. (Nashua, N.H.), and were also used as received. Phosphate buffered saline packets were purchased from Sigma and diluted to the desired concentration (150 mM, pH=7.4) with distilled water. Dulbecco's modified eagle medium (DMEM), BSA (fraction V), and fibronectin were purchased from Gibco (Life Technologies, Rockville, Md.); we added 5 $\mu$M HEPES (JRH Biosciences, Lenexa, Kans.) to the medium. Sodium dodecyl sulfate (SDS) was purchased from Bio Rad (Hercules, Calif.). Gelatin was purchased from DIFCO Laboratories (Detroit, Mich.). Para-formaldehyde was purchased from Electron Microscopy Sciences (Ft. Washington, Pa.).

Substrates.

We patterned cells on the surfaces of Petri dishes, PDMS, glass slides, silicon (<110>, native oxide). Unless specified otherwise, we always use Petri dishes as the substrates.

EXAMPLE 1

Fabrication of Masking System

Fabrication of Patterned Photoresist Structures and Membranes.

Figure 3:
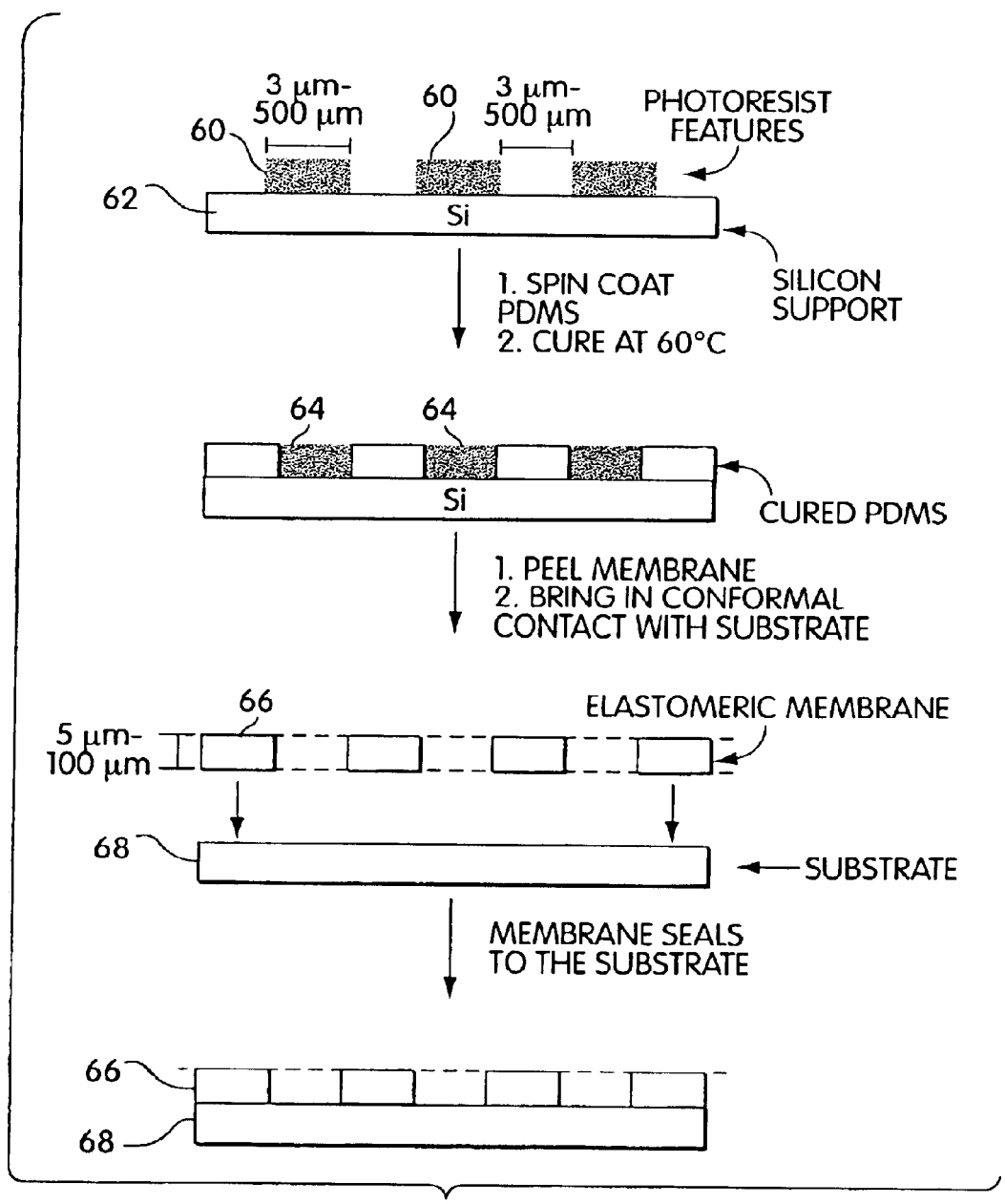
FIG. 3 shows a schematic diagram for the fabrication of a masking system for use in the invention.

With reference to FIG. 3, arrays of cylindrical posts of photoresist 60 were fabricated on silicon wafers 62 using standard photolithographic techniques and rigid chrome masks. Arrays of square features were fabricated using transparencies as photomasks. We used procedures well-known in the art to fabricate features there were 50 $\mu$m high.

Fabrication of Masking Systems.

Figure 4:
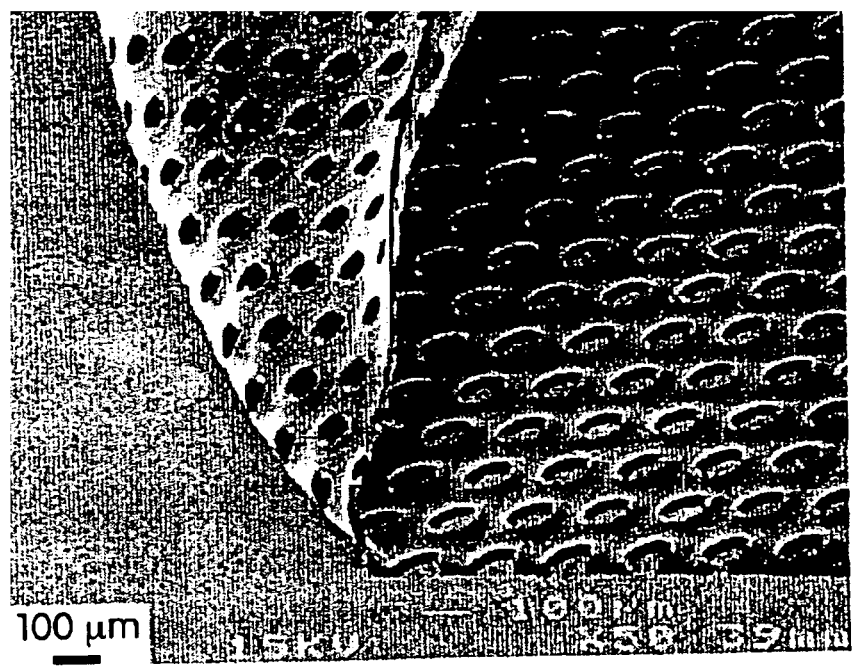
FIG. 4 shows a photocopy of a scanning electron micrograph of a masking system for use in the invention having channels shaped as holes having a diameter of about 100 $\mu$m.

Elastomeric polymer membranes were fabricated using the procedure described by Jackman et al. (Jackman et al., Langmuir, vol. 15, pp. 2973–2984, (1999)). The PDMS prepolymer 64 (mixed in a 10:1 ratio with a crosslinking catalyst) was spin-coated on the bas-relief of patterned photoresist using parameters known to produce a film that was thinner than the height of the features of photoresist. For features that were 50 $\mu$m tall, we spin-coated PDMS prepolymer at 3000 rpm for 60 sec to generate a film that was approximately 45 $\mu$m thick. The PDMS films were cured for 2 h at 60° C. A thick layer of PDMS prepolymer was added to the edges of the membranes in dropwise fashion; after curing, this layer of PDMS provided a frame that would support the substrates; we typically used pieces that were 2×2 cm. The films were kept at 60° C. overnight. Prior to use in cell culture, we removed low molecular weight polymer from the membranes by soaking them in dichloromethane for 12 h. The membranes were then soaked in ethanol for 1 hour and dried in an oven at 60° C. for 12 hours. The membranes 66 were removed from their supports photoresist posts, cylindrical or square, on silicon) using tweezers and they were then cut to the desired sizes along the edges of the support. FIG. 4 shows a photocopy of a scanning electron micrograph of a membrane with 100 $\mu$m circular holes. The membrane is approximately 50 $\mu$m thick. The membrane is curved upwards while being removed from the surface as in the peeling step in FIGS. 1 and 2. This image illustrates the elastomeric properties of the membrane. The membranes generally come into conformal contact with the substrates 68. In cases when the membranes were not flat on the surface and adhered to themselves, we placed a drop of ethanol on them to facilitate the formation of a flat seal. The ethanol wets the surface of the membrane preferentially and it allows it to become flat; evaporation of the ethanol leaves the membranes flat on the substrates. The membranes were ready for use after evaporation of the ethanol.

For biological experiments, low molecular weight organic substances can be extracted from the membranes by soaking the membranes in dichloromethane for several hours (overnight) followed by drying at 60° C. for several hours (overnight). The membranes are then placed onto Petri dishes and covered with a few drops of absolute ethanol. Ethanol can help decrease the tendency of the membranes to adhere to themselves and facilitate a formation of conformal contact between the membrane and the surface of the substrate. Ethanol also sterilizes the membranes and the surfaces of the substrates. Alternatively, a conformal seal with a substrate can be achieved when the membrane is positioned on the substrate in the presence of PBS buffer. This buffer also affords maintaining the hydration of the layer of BSA. A layer of BSA that has been allowed to dry does not resist the attachment of cells as well as one that has been kept hydrated. In the Examples, substrates are exposed to suspensions of bovine capillary endothelial (BCE) cells.

Typically a 2 mL suspension of 25,000 cells/mL in a dish having an area of 962 mm².

Procedure Used to Wash the Membrane After Use in Cell Culture.

The membranes were kept in buffered SDS (10 mg/mL, PBS at pH=7.4) for 30 min at room temperature and 30 min at 90° C., followed by extensive rinsing with deionized water and ethanol. The membranes were then extracted with dichloromethane for 12 hours and dried at 60° C. for 12 hours. These membranes (like other microscopic structures made of PDMS) can also be autoclaved for 20 min (121° C., 115 kPa).

EXAMPLE 2

Surface Modification a) Pre-Coating the Membrane With a Cell Adhesion Inhibitor.

In a laminar flow hood, the membranes were placed on the surface of a sterile Petri dish with a few drops of ethanol. The liquid sterilized the membranes by killing bacteria. Drops of a buffered solution of BSA (1% w/v, in PBS or DMEM at pH=7.4) were placed on the membrane to cover the holes, in a manner schematically described in FIG. 2. Since the liquid did not fill the hydrophobic pores, vacuum was applied (~30 sec) and released (~500 mTorr) twice to extract the air trapped in the pores. BSA was allowed to adsorb to the surfaces for 15 min. The substrates were then rinsed three times with PBS; the membranes were peeled from the support in the presence of PBS, and transferred to a clean Petri dish covered with PBS to help seal the membrane onto the dish.

b) Patterning Proteins on Substrates.

Drops of a cell-adhesion promoter, buffered fibronectin (50 μg/mL, PBS with pH=7.4) or gelatin (1.5% w/v, PBS with pH=7.4) solutions were placed on a membrane adhered to a substrate. Vacuum was applied (ca. 30 sec) and released twice to extract the air trapped in the pores. The protein was allowed to adsorb to the surfaces for 1 hr (in the case of fibronectin) or for 15 min (in the case of gelatin). The assembly of the membrane and substrate was then rinsed with buffer 3 times. The membrane was removed from the surface with a pair of tweezers, in the presence of culture media that contained 1% (w/v) BSA. After 15 min, fresh media was introduced into the dish, followed by a suspension of cells.

Immunofluorescent Staining of Adsorbed FN.

The substrates coated with FN were exposed to 4% (v/v) PFA in PBS buffer (pH=7.4) for 20 min, and then immersed in a solution of rabbit anti-human fibronectin IgG (Sigma, 5 μg/mL) for 1 hour. The substrates were rinsed twice with PBS containing 0.1% (w/v) BSA and 0.1% (v/v) Triton X-100, and placed in contact with 100 μL of Texas Redo-labeled goat anti-rabbit IgG (Amersham Life Sciences, 50 μg/mL) for 1 hour; the samples were then rinsed, and sealed onto microscope slides with Fluoromount-G (Southern Biotechnology, Inc.).

EXAMPLE 3

Cell Culture a) Growth and Attachment.

Bovine adrenal capillary endothelial (BCE) cells were cultured under 10% $CO_2$ on cell culture Petri dishes (Falcon) coated with gelatin in DMEM containing 10% calf serum, 2 mM glutamine, 100 μg/mL streptomycin, 100 μg/mL penicillin, and 1 ng/mL basic fibroblast growth factor (bFGF).[2] Prior to incubation with the patterned substrates prepared using MEMPAT, cells were dissociated from culture plates with trypsin-EDTA and washed in DMEM containing 1% BSA (BSA/DMEM). The suspension of cells (typically 25,000 cells/mL, 2 mL total volume) was placed on the substrates in chemically defined medium (10 μg/mL high density lipoprotein, 5 μg/mL transferrin, 5 ng/mL basic fibroblast growth factor in 1% BSA/DMEM) and incubated in 10% $CO_2$ at 37° C.

b) Fixing and Staining Cells.

Substrates that contained cells were fixed with PFA for 20 min and washed with PBS. The substrates were then washed with methanol for 1 min, and stained with Coomassie Blue (5 mg/mL in 40% v/v methanol, 10% v/v acetic acid, and 50% v/v water) for 30 sec; they were then rinsed with distilled water and dried in air.

Procedures Used to Study Cell Spreading.

Cells were allowed to attach to patterns of gelatin or FN defined by the holes of the BSA-coated membranes. After 7–24 hours, the assembly defined by the membrane, the substrate, and the attached cells was rinsed with PBS buffer three times to remove BSA from the solution and it was then immersed in a PBS solution of gelatin (1.5% w/v). The membrane was peeled gently from the surface with a pair of tweezers and the substrates were incubated for 15 min to adsorb gelatin on the areas of the surface that were protected by the membrane. The substrates were then rinsed once with culture medium (DMEM) before being placed in the incubator for ca. 4 hours, to allow the cells to spread onto the previously protected areas of the substrates.

Characterization of Damage to Cells.

Membranes were gently removed from substrates that presented attached cells. The attached cells were incubated with a solution of propidium iodide in culture medium (10 μg/mL) for 15 minutes. The cells were imaged with a fluorescence microscope immediately after rinsing the samples twice with culture medium at 37° C. The intensity of the fluorescence of propidium iodide decreased as the dye diffused out of the cells over the course of two hours; this diffusion into the medium also decreased the contrast obtained in the micrographs.

Microscopy.

a) Phase contrast and fluorescence microscopy were performed with a Nikon Axiophot equipped with a 35 mm camera. The developed negatives or slides were scanned into a digital format with a Nikon LS-400 slide scanner. Images were processed only by performing operations uniformly on the entire image; we typically converted the color images to black and white and enhanced the contrast to ensure that the fine features of the cell structure would appear in the version of the figure printed in the journal.

b) SEM micrographs were obtained on a JEOL JSM-6400 scanning electron microscope operating at 15 keV.

EXAMPLE 4

Figure 5A:
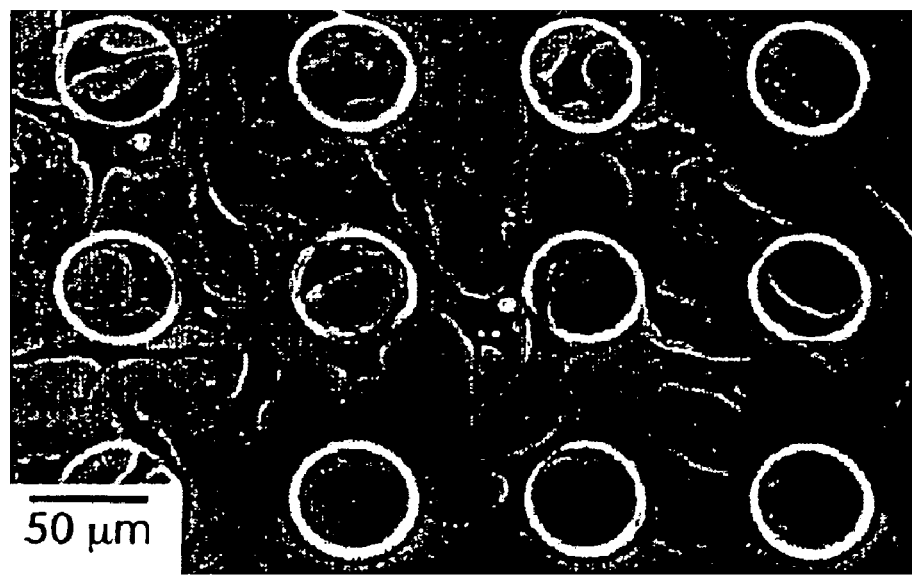
FIG. 5A shows a photocopy of a fluorescence micrograph displaying comparative results of completely coating a substrate with a cell-adhesion protein followed by the addition of cells over the entire assembly.
Figure 5B:
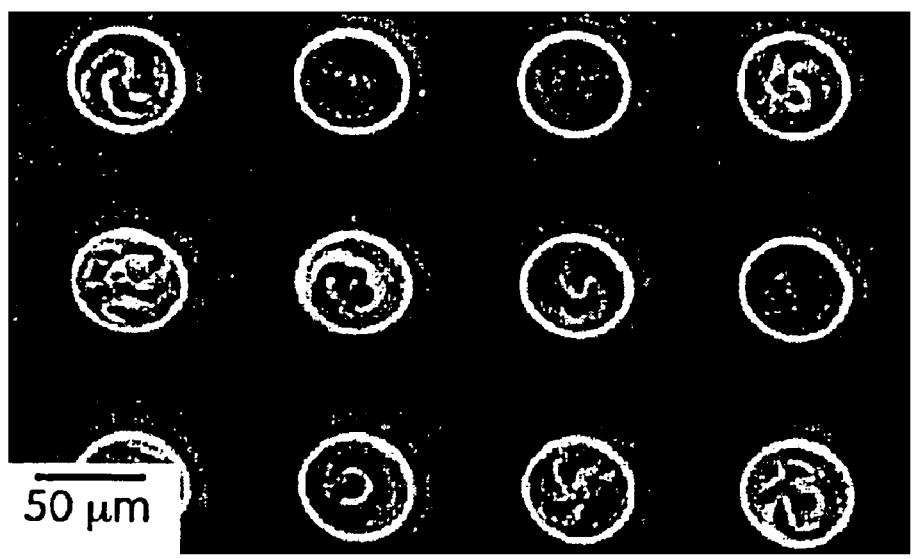
FIG. 5B shows a photocopy of a fluorescence micrograph of the cells adhered selectively to the surface of the substrate.

Comparison of Pre-Coating Masking System With Cell-Adhesion Inhibitor Verses No Pre-Coating FIGS. 5A and 5D show photocopies of optical micrographs displaying the result of coating the membranes with different proteins. This process helps to determine whether cells attach to the substrate and the membranes or only to the substrate. FIG. 5A shows cells that are adhered over the entire assembly of membrane and substrate that was coated with FN as described above without use of a cell-adhesion inhibitor coating of the masking system. FIG. 5B shows that cells adhere selectively to the surface of the substrate that was coated with FN using a membrane that is pre-coated with BSA (see FIG. 2). The cells do not attach to the membrane.

EXAMPLE 5

Figure 6A:
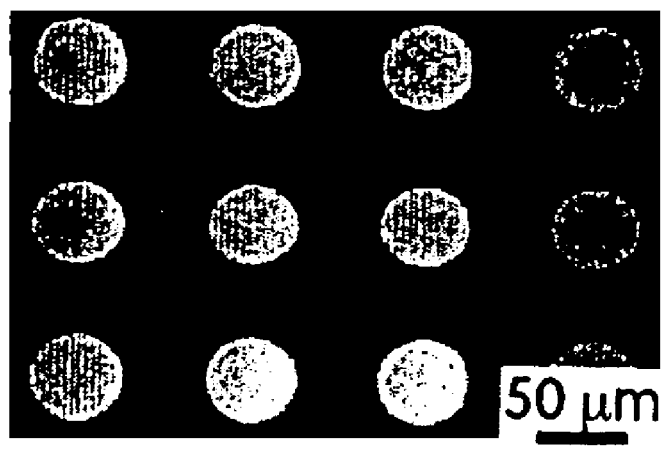
FIG. 6A shows a photocopy of a fluorescence micrograph displaying a pattern of fibronectin after peeling the masking system in a process of the invention.
Figure 6B:
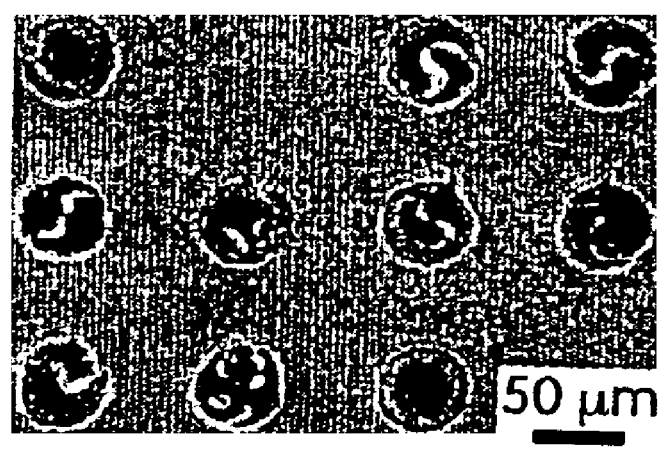
FIG. 6B shows a photocopy of a fluorescence micrograph displaying a pattern of cells adhered to circular islands of fibronectin of FIG. 6A.

FIG. 6A shows a photocopy of a fluorescence image displaying a pattern of FN generated on a bacteriological petri dish using the masking system technique described above, following the application and release of vacuum. After an incubation of 1 hour followed by three rinsing steps, the membrane is removed from the substrate in the presence of culture medium that contained BSA or any other BSA-containing solution (see Example 1). Thus, the membrane is removed after the adsorption of protein and before attachment of cells. This method provides a pattern of cells while exposing the rest of the surface for the adsorption of another agent, e.g., a protein (see FIG. 7). The FN pattern on the surface is incubated with fluorescently labeled antibodies that make the FN appear light gray in fluorescence microscopy. FIG. 6B shows a pattern of cells adhered to circular islands of FN with 50 μm in diameter, prepared with the same method as for FIG. 6A.

EXAMPLE 6

Figure 7A:
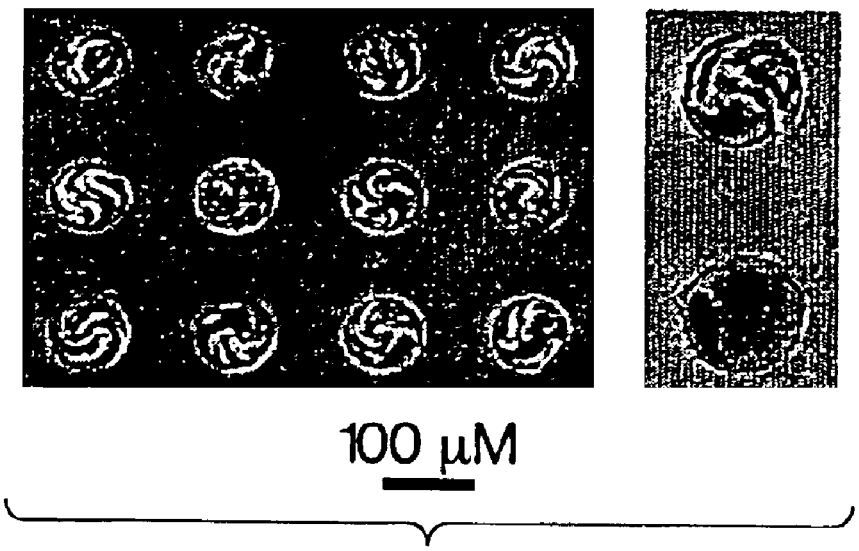
FIG. 7A shows a photocopy of an optical micrograph of cells patterned on circular islands having a diameter of about 100 µm according to the invention.
Figure 7B:
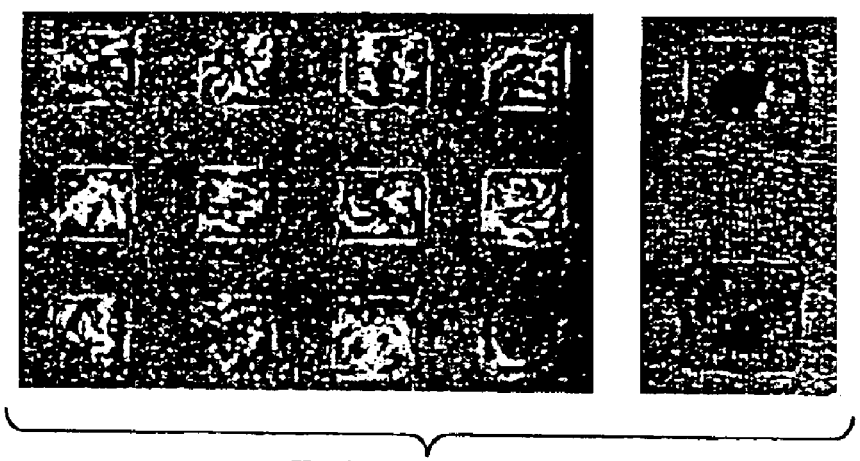
FIG. 7B shows a photocopy of an optical micrograph of cells patterned on square islands having a sides of a length of about 100 µm according to the invention.

FIGS. 7A and 7B show photocopies of optical micrographs of cells patterned on a bacteriological petri dish that presented islands of FN that were generated using the technique of Example 2. The membrane is coated with BSA and then placed on a clean petri dish and exposed to a solution of FN (50 mg/mL in PBS) as described in Example 2. The membrane and the substrate are covered with a suspension of cells for 24 hours. The membrane is removed and the cells are fixed and stained to show the nuclei and parts of the cytoskeleton. The efficiency of patterning is comparable to that achieved with MEMPAT (see FIG. 6). FIG. 7A shows cells patterned on circular islands 100 μm in diameter. FIG. 7B shows cells patterned on square islands with 100 μm sides.

EXAMPLE 7

FIG. 8 shows the results of pre-coating membranes with BSA to avoid damage to the membranes of cells during membrane removal, versus no pre-coating. A membrane is placed in conformal contact with a substrate surface and the membrane and the surface of the substrate are coated with fibronectin (FN). A suspension of BCE cells is then placed in contact with such a surface and the membrane is removed. Cells adhere to the substrate specifically or to the substrate and the membrane. After 24 hours in culture, the membranes are removed from both types of samples and the cells that remain attached to the surface of the substrate are incubated with propidium iodide dissolved in culture medium (10 μg/mL), for 15 minutes; this fluorescent agent only penetrates the membranes of damaged cells. The samples are imaged after rinsing with culture medium.

Micrographs on the left-hand side of FIG. 8 are obtained by phase-contrast microscopy. Micrographs on the right-hand side of FIG. 8 are obtained by fluorescence microscopy. For the fluorescence micrographs, cells are incubated with propidium iodide after membrane removal.

Figure 8A:
FIG. 8A shows a photocopy of a phase-contrast micrograph and a fluorescence micrograph of cells patterned with a BSA pre-coated membrane for features having a diameter of 250 µm in a process of the invention.
Figure 8B:
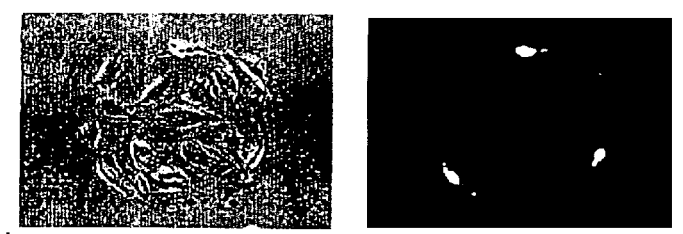
FIG. 8B shows a photocopy of a phase-contrast micrograph and a fluorescence micrograph of cells patterned without a BSA pre-coated membrane for features having a diameter of 250 µm.
Figure 8C:
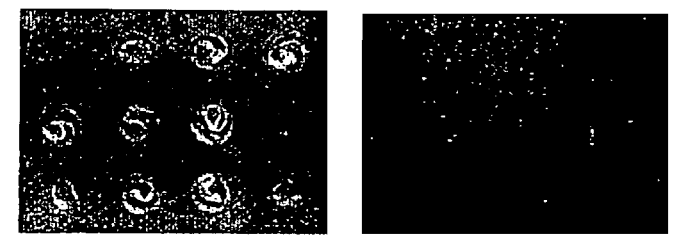
FIG. 8C shows a phase-contrast micrograph and a fluorescence micrograph of cells patterned with a BSA pre-coated membrane for features having a diameter of 100 µm.

FIGS. 8A and 8C show BCE cells patterned on a substrate through a membrane which was pre-coated with BSA using the procedure of Example 2. After removal of the membrane, the cells were incubated with propidium iodide. FIG. 8A shows a pattern of features having a diameter of 250 μm whereas FIG. 8C shows a pattern having features of a diameter of 100 μm. The corresponding fluorescence micrograph show that no cells internalize the fluorescent dye indicating that the cell membranes were not damaged.

Figure 8D:
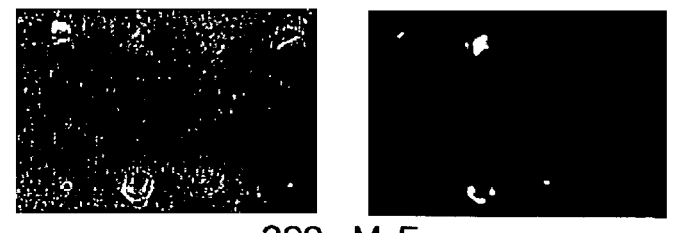
FIG. 8D shows a phase-contrast micrograph and a fluorescence micrograph of cells patterned without a BSA pre-coated membrane for features having a diameter of 100 µm.

FIGS. 8B and 8D show the results of a membrane and substrate coated with fibronectin where the membrane was not pre-coated with BSA, as described in Example 1. FIG. 8B shows a pattern having features of a diameter 250 μm whereas FIG. 8D shows a pattern having features of a diameter 100 μm. Removal of the membrane in FIGS. 8B and 8D show a poorly defined pattern of cells. Many of the adhered cells appear to be damaged in the corresponding fluorescence micrographs.

Figure 8E:
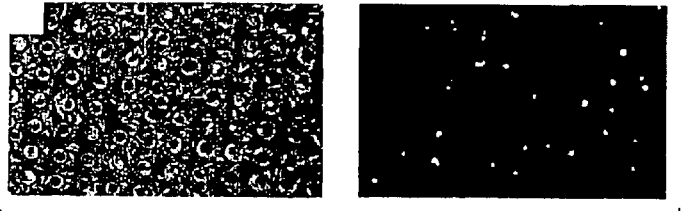
FIG. 8E shows a phase-contrast micrograph of a surface of the membrane removed from the process of FIG. 8B, showing attached cells.

FIG. 8E shows a surface of a membrane that was used in FIG. 8B after removal of the membrane from the surface, where the surface of the membrane is covered by attached cells. Many cells also adhere to the walls of the holes. A fluorescence micrograph of the membrane revealed that many of the cells attached in the holes presented damaged membranes.

EXAMPLE 8

Figure 9A:
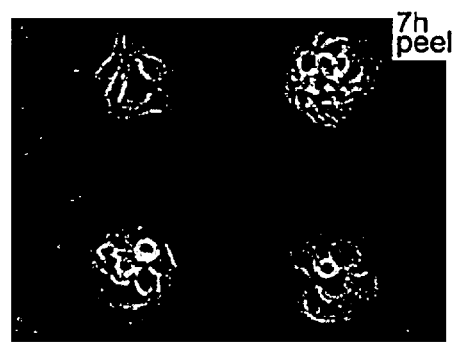
FIGS. 9A–D show photocopies of scanning electron micrographs displaying the results of cell spreading after (a) 7 h, (b) 8.2 h, (c) 9.5 h, and (d) 11 h.
Figure 9B:
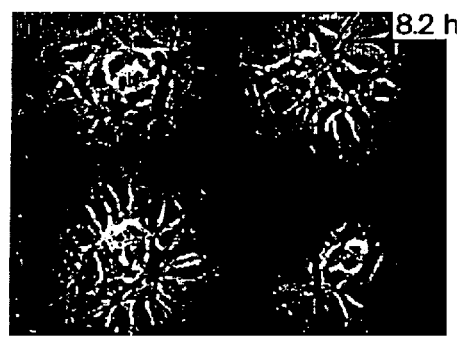
Figure 9C:
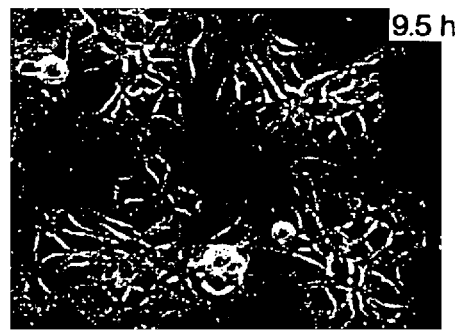
Figure 9D:
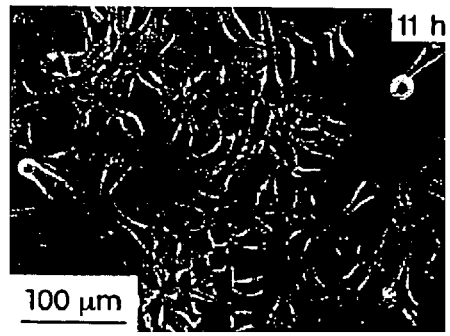

This example provides a demonstration that the techniques of the invention allow the study of cell spreading. Cells are patterned on petri dishes using BSA-coated membranes as described in Example 2. The cells were allowed to spread on the substrate in conformal contact with a membrane for 6–20 hours until the cells covered the entire area exposed by a channel of the membrane. The membrane was removed from the substrate in the presence of a solution of gelatin (free of all BSA) and incubated for 20 minutes. This procedure coats the areas of the substrate that had previously been covered by the membrane with a layer of adhesive protein. After replacing the solution of gelatin with culture medium, the cells were incubated. For varying intervals over a period of 7 hours to 11 hours and at each indicated time from the beginning of the experiment, one sample is fixed and stained. FIGS. 9A–D show photocopies of scanning electron micrograph images displaying an area that is representative of the entire sample. FIG. 9A shows a discrete pattern of cells. As the cells are allowed to spread as shown in FIGS. 9B and 9C, eventually the cells spread over the entire portion of the substrate as shown in FIG. 9D.

Those skilled in the art would readily appreciate that all parameters listed herein are meant to be examples and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described.

What is claimed:

1. A method for patterning cells, comprising:
providing a masking system, the masking system comprising a flexible cohesive mask, and the masking system including a first surface, an opposing second surface, and a plurality of channels passing through the masking system connecting the first surface with the second surface;
pre-coating a second agent onto the second surface and the plurality of channels of the masking system, wherein the first surface of the masking system is free of the second agent;

thereafter, shielding a first portion of a surface of an article with the masking system by contacting the first surface of the masking system with the article, wherein the flexible cohesive mask is in conformal contact with the surface of the article;

applying a first agent through a channel within the masking system to a second portion of the surface of the article while preventing application of the first agent to the first portion of the surface of the article, the channel being one of the plurality of channels;

thereafter, applying cells through the channel within the masking system to the second portion of the surface of the article so the cells contact the first agent while preventing application of the cells to the first portion of the surface of the article; and removing the masking system from the first portion of the surface of the article.

2. The method of claim 1, wherein the first portion of the surface of the article is contiguous with the second portion.

3. The method of claim 1, wherein the channel has a dimension for controlling the growth of a single cell.

4. The method of claim 1, wherein the first agent is a cell-adhesion promoter.

5. The method of claim 4, wherein the first agent is a protein.

6. The method of claim 5, wherein the protein is fibronectin.

7. The method of claim 4, wherein the second agent is a cell-adhesion inhibitor.

8. The method of claim 7, further comprising adding a third agent to the first portion of the surface of the article.

9. The method of claim 8, further comprising allowing the cells applied to the first agent to spread onto the third agent.

10. The method of claim 8, wherein the first agent is a first cell-adhesion promoter and the third agent is a second cell-adhesion promoter.

11. The method of claim 10, further comprising adding cells of a second type to the third agent.

* * * * *